(12) United States Patent
Schröder et al.

(10) Patent No.: US 7,199,592 B2
(45) Date of Patent: Apr. 3, 2007

(54) METHOD AND APPARATUS FOR APPLYING MICROWAVES TO MEASURE THE MOISTURE CONTENT OF MATERIAL

(75) Inventors: Dierk Schröder, Hamburg (DE);
Norbert Hohenstein, Glinde (DE);
Peter Schreiber, Reinbek (DE);
Andreas Noack, Drage (DE); Jörg Tobias, Drage (DE)

(73) Assignee: Hauni Maschinenbau AG, Hamburg (DE)

( * ) Notice: Subject to any disclaimer, the term of this patent is extended or adjusted under 35 U.S.C. 154(b) by 99 days.

(21) Appl. No.: 10/161,611

(22) Filed: Jun. 5, 2002

(65) Prior Publication Data

US 2002/0149378 A1    Oct. 17, 2002

Related U.S. Application Data

(63) Continuation of application No. 09/447,794, filed on Nov. 23, 1999, now Pat. No. 6,417,676.

(30) Foreign Application Priority Data

Nov. 26, 1998    (DE) .................................. 198 54 550

(51) Int. Cl.
*G01R 27/04* (2006.01)
*G01R 27/32* (2006.01)

(52) U.S. Cl. .................................................... 324/640

(58) Field of Classification Search ................ 324/640, 324/637, 639, 633, 634, 700; 236/47, 46 R; 205/776.5; 428/209

See application file for complete search history.

(56) References Cited

U.S. PATENT DOCUMENTS 3,529,267 A    9/1970 Gunderson et al.
3,946,308 A    3/1976 Miura et al.
4,042,879 A    8/1977 Ho et al.
4,104,584 A    8/1978 Miyai et al.
4,452,256 A    6/1984 Wochnowski et al.
4,488,132 A   12/1984 Collins et al.
4,674,325 A    6/1987 Kiyobe et al.
4,748,427 A    5/1988 Buoli
4,862,110 A *  8/1989 Charbonnier ................. 331/70

(Continued)

FOREIGN PATENT DOCUMENTS

DE    3622956    2/1988

(Continued)

OTHER PUBLICATIONS

"Apparatus for Making Filter Cigarettes," Research Disclosure, Mar. 1998, pp. 193-194.

*Primary Examiner*—James C Kerveros
(74) *Attorney, Agent, or Firm*—Venable LLP; Catherine M. Voorhees; Lars H. Genieser

(57) ABSTRACT

Apparatus for ascertaining the mass and/or the moisture content of successive increments of a running rod containing tobacco and/or filter material for tobacco smoke has a resonator housing with a cylindrical internal chamber which is disposed between an inlet and an outlet and wherein the rod is exposed to microwaves. The housing is made of a metallic material having a low thermal expansion coefficient, and its internal surface is lined with gold or another corrosion resistant substance. A protective plastic tube establishes a path for the rod from the inlet, across the chamber and into the outlet of the resonator housing.

1 Claim, 1 Drawing Sheet

U.S. PATENT DOCUMENTS

| | | | |
|---|---|---|---|
| 4,885,527 A | | 12/1989 | Lacombe et al. |
| 4,991,915 A | | 2/1991 | Thompson et al. |
| 5,041,800 A | * | 8/1991 | Long et al. .................... 331/69 |
| 5,103,180 A | | 4/1992 | Lahitte et al. |
| 5,369,368 A | | 11/1994 | Kassen et al. |
| 5,397,993 A | | 3/1995 | Tews et al. |
| 5,521,438 A | * | 5/1996 | Okamoto et al. ........... 257/703 |
| 5,602,865 A | * | 2/1997 | Laakmann .................... 372/82 |
| 5,736,864 A | * | 4/1998 | Moller ....................... 324/633 |
| 5,838,158 A | | 11/1998 | Beck et al. |
| 5,925,431 A | * | 7/1999 | Schoenfelder ............. 428/40.1 |
| 6,398,118 B1 | * | 6/2002 | Rosen et al. ................ 236/49.3 |
| 6,417,676 B1 | * | 7/2002 | Schroder et al. ............ 324/640 |
| 6,476,619 B1 | * | 11/2002 | Moshe et al. ................ 324/634 |

FOREIGN PATENT DOCUMENTS

| | | |
|---|---|---|
| EP | 0 292 571 A1 | 11/1988 |
| EP | 0 372 992 A2 | 6/1990 |
| EP | 0 716 303 A2 | 6/1996 |
| EP | 0 758 085 A2 | 1/1997 |
| EP | 0 758 085 A2 | 2/1997 |
| EP | 0 789 237 A1 | 8/1997 |
| EP | 0 791 823 A2 | 8/1997 |
| EP | 0 791 823 A3 | 12/1997 |
| EP | 0 758 085 A3 | 9/1999 |
| FR | 2556470 A1 | 6/1985 |

* cited by examiner

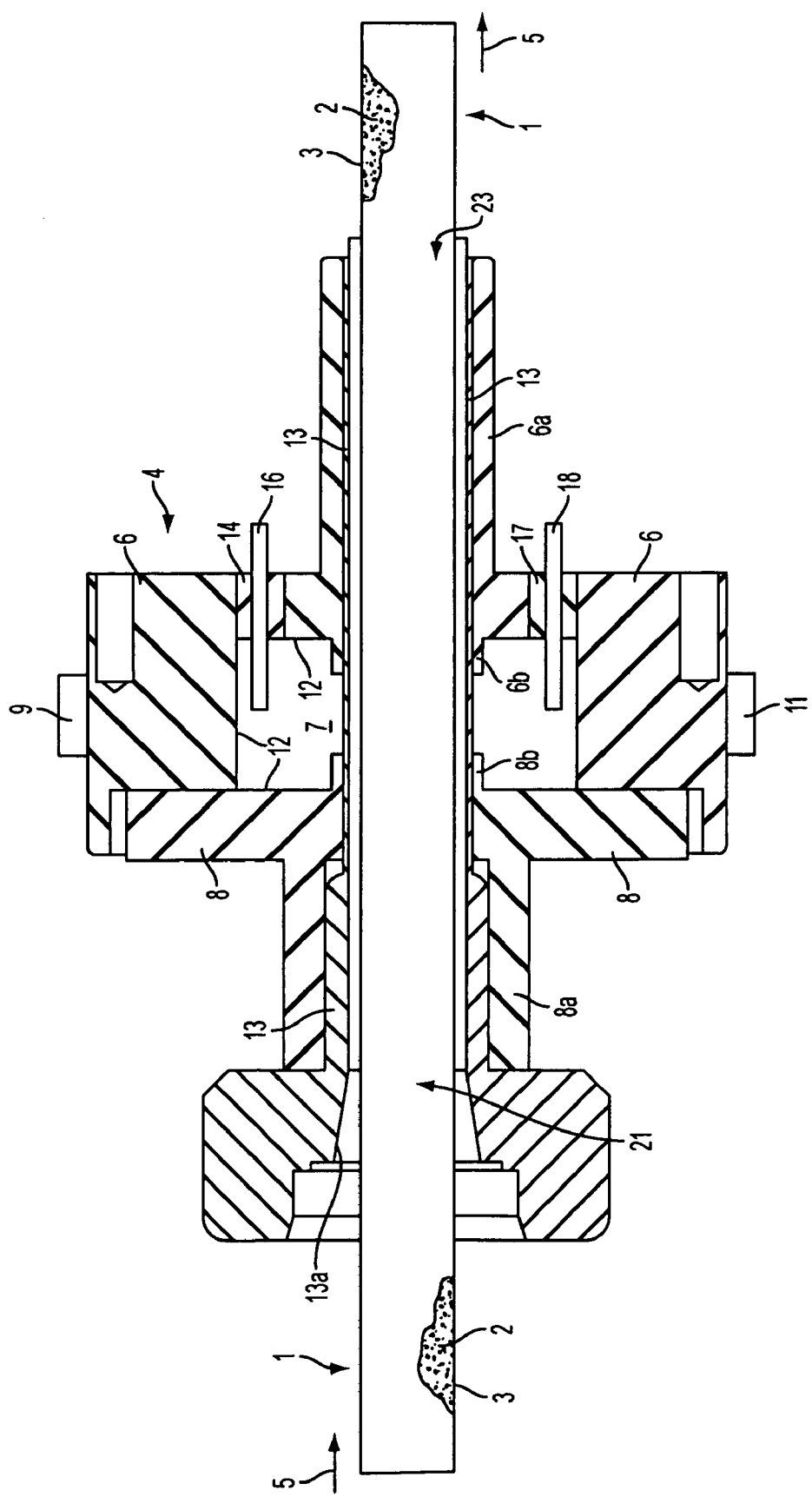

METHOD AND APPARATUS FOR APPLYING MICROWAVES TO MEASURE THE MOISTURE CONTENT OF MATERIAL

CROSS-REFERENCE TO RELATED CASES

This application is a continuation of application Ser. No. 09/447,794 filed Nov. 23, 1999 (now U.S. Pat. No. 6,417,676, issued Jul. 9, 2002), which is incorporated herein by reference.

This application claims the priority of German patent application Ser. No. 198 54 550.9 Nov. 26, 1998. The disclosure of the above-referenced German patent application, as well as that of each US and foreign patent and patent application mentioned in the specification of the present application, is incorporated herein by reference.

BACKGROUND OF THE INVENTION

The present invention relates to improvements in apparatus for ascertaining certain characteristics of substantially rod-shaped commodities. More specifically, the invention relates to improvements in apparatus which can be utilized to ascertain the mass and/or the moisture content of rod-shaped commodities which are moved lengthwise through the internal chamber of a housing wherein successive increments of the moving commodities are subjected to the action of microwaves. The commodities constitute, or can constitute, rod-shaped products of the tobacco processing industry, for example, rod-like fillers of shredded tobacco of the type contained in plain or filter cigarettes, cigarillo tobacco or cigar tobacco. Furthermore the commodities can constitute wrapped fillers constituting filter material (such as paper and/or cellulose acetate) for tobacco smoke.

Commonly owned published European patent application Serial No.0791 823 A2 and the corresponding U. S. Pat. No. 6,163,158 disclose an apparatus wherein a continuous rod (such rod can comprise a filler of shredded tobacco confined in a tubular envelope of cigarette paper) is caused to advance through a resonator housing having an internal chamber where the rod is subjected to the action of microwaves in order to ascertain the mass and/or the moisture content of the filler. The resonator housing consists of a metallic material. Changes of the characteristics of the microwaves which have been influenced by the moving rod in the internal chamber of the resonator housing are evaluated by one or more suitable circuits (such circuit or circuits can also ascertain the characteristics of the microwaves when the internal chamber of the resonator housing is empty) for the purpose of ascertaining and furnishing information pertaining to the mass and/or the moisture content of unit lengths of the moving rod.

OBJECTS OF THE INVENTION

An object of the invention is to provide a novel and improved resonator housing for use in apparatus of the type disclosed in the published European patent application Serial No. 0 791 823 A2.

Another object of the invention is to provide a resonator housing which contributes to the accuracy and/or sensitivity of the apparatus.

A further object of the invention is to provide the apparatus with novel and improved apparatus for defining a path for lengthwise movement of rod-shaped commodities through the internal chamber of the resonator housing.

An additional object of the invention is to provide novel and improved apparatus for maintaining the temperature of the resonator housing within an optimum range to ensure highly accurate measurements pertaining to the mass and/or moisture content of successive increments of the moving commodity or commodities.

Still another object of the invention is to provide a novel method of and novel apparatus for prolonging the useful life of the resonator housing.

A further object of the invention is to provide a resonator housing that is not affected or is not appreciably affected by the so-called skin effect which is a factor affecting the measurements carried out by apparatus employing conventional resonator housings.

Another object of the invention is to provide the apparatus with novel and improved materials for preventing corrosion of the internal and/or external surface of the resonator housing.

SUMMARY OF THE INVENTION

One feature of the present invention resides in the provision of an apparatus which can be utilized to ascertain the characteristics of moving elongated rod-shaped commodities of the tobacco processing industry by exposure to microwaves. The apparatus comprises a resonator housing having an inlet for admission and an outlet for evacuation of commodities, and at least a portion of the housing consists of a material having a low thermal expansion coefficient. The exposure of commodities to microwaves takes place in an internal chamber which is disposed between the inlet and the outlet of the housing, and such exposure normally serves to ascertain the mass and/or the moisture content of commodities.

The material of the resonator housing can constitute an alloy, e.g., an alloy containing approximately 64% of iron and approximately 36% of nickel.

In the absence of any undertakings to the contrary, the temperature of the resonator housing varies or is likely to vary when the apparatus is in use. Therefore, the apparatus preferably further comprises a regulator for regulating the temperature of the housing; the regulator preferably maintains the temperature of the housing at least close to a preselected value in actual use of the apparatus. The regulator can comprise a thermometer which serves to generate signals denoting the temperature of the housing, and at least one transistor which is designed to dissipate (in response to signals from the thermometer) heat at a rate proportional to variations of the temperature of the housing. It is preferred to resort to a preselected value which is higher than the temperature of the atmosphere around the housing.

The internal chamber is preferably configurated in such a way that it is symmetrical with reference to the longitudinal axis of the rod-shaped commodity being moved through the internal chamber from the inlet to and through and beyond the outlet of the resonator housing. For example, the housing can be provided with an at least substantially cylindrical internal chamber.

The internal chamber can be, and preferably is, bounded at least in part by a corrosion resistant substance. Such substance can constitute a liner which surrounds a portion of or the entire internal chamber. The substance of the liner can contain at least one metal; for example, the liner can contain or can consist of gold. It is advisable to select the metal of the corrosion resistant substance in such a way that the latter is a good conductor of electric current.

It is further advisable to provide the resonator housing with a liner which consists of a corrosion resistant material and coats at least a portion of the external surface of the housing. Such external liner can contain or consist of gold.

The apparatus can be equipped with a protective tube which surrounds a path for the commodities being moved through the housing in a direction from the inlet toward the outlet. The protective tube can be made of or it can contain a suitable plastic material, for example, a polyaryletherketone and preferably a polyaryletheretherketone. In accordance with a feature of the invention, the protective tube has a receiving portion which is disposed at the inlet of the resonator housing and defines a passage which diverges in a direction away from the outlet.

The housing can be provided with an extension which surrounds the inlet and/or the outlet and serves to oppose issuance or escape of microwaves from the internal chamber between the inlet and the outlet of the housing.

Still further, the housing can comprise a tubular extension which is provided at the inlet and/or at the outlet, i.e., in the internal chamber, and which defines a portion of the aforementioned path for movement of commodities from the inlet to the outlet.

The apparatus further comprises microwave generator components for admitting microwaves from the generator into the internal chamber, preferably microwaves having at least two different frequencies, and a circuit having a comparator for comparing a first resonance curve which is influenced by the commodities in the housing with a second resonance curve which is not influenced by the commodities in the housing to thus ascertain a shift of frequency of the first resonance curve by the commodities. The circuit can further comprise a comparator for comparing the amplitudes of the first and second resonance curves for the purpose of ascertaining the extent of damping of the first curve by the commodities. The aforementioned different frequencies are preferably associated with a downwardly sloping flank of a resonance curve.

Another feature of the invention resides in the provision of an apparatus which serves to ascertain the characteristics of moving elongated rod-shaped commodities of the tobacco processing industry by exposure to microwaves. The improved apparatus comprises a metallic housing having an inlet for admission of commodities, an outlet for evacuation of commodities, and an internal chamber disposed between the inlet and the outlet to provide or establish a region for exposure of commodities to microwaves in order to ascertain at least one of (a) the mass and (b) the moisture content of commodities. The temperature of the housing is variable when the apparatus is in use, and the apparatus further comprises a regulator for regulating the temperature of the housing while the apparatus is in use. The regulator can be designed, assembled and operated in a manner as already outlined hereinbefore.

A further feature of the invention resides in the provision of an apparatus for ascertaining the characteristics of moving elongated rod-shaped commodities of the tobacco processing industry by exposure to microwaves. The improved apparatus comprises a metallic housing having an inlet for admission of commodities, an outlet for evacuation of commodities and an internal chamber which is disposed between the inlet and the outlet to provide a region for exposure of commodities to microwaves in order to ascertain the mass and/or the moisture content of commodities. The apparatus further comprises a corrosion resistant substance which bounds at least a portion of the internal chamber. The configuration, size and material of the corrosion resistant substance can be selected as already described hereinbefore.

An additional feature of the invention resides in the provision of an apparatus for ascertaining the characteristics of moving elongated rod-shaped commodities of the tobacco processing industry by exposure to microwaves. The apparatus comprises a metallic resonator housing having an inlet for admission of commodities, an outlet for evacuation of commodities and an internal chamber disposed between the inlet and the outlet to provide a region for exposure of commodities to microwaves to thus ascertain the mass and/or the moisture content of commodities. The improved apparatus further comprises a protective tube which surrounds a path for commodities being moved through the housing from the inlet, through the internal chamber and to and beyond the outlet. The material and the configuration of the protective tube can be selected in a manner and for the purposes as pointed out hereinbefore.

The novel features which are considered as characteristic of the invention are set forth in particular in the appended claims. The improved apparatus itself, however, both as to its construction and the modes of constructing, assembling and operating the same, together with numerous additional important and advantageous features and attributes thereof, will be best understood upon perusal of the following detailed description of certain presently preferred specific embodiments with reference to the accompanying drawing.

BRIEF DESCRIPTION OF THE DRAWING

The single FIGURE of the drawing is a fragmentary central longitudinal sectional view of an apparatus which embodies the features of the present invention and is utilized to subject a running wrapped filler of tobacco or filter material for tobacco smoke to the action of microwaves to ascertain the mass and/or the moisture content of the filler.

DESCRIPTION OF PREFERRED EMBODIMENTS

The measuring apparatus a portion of which is shown in the drawing is in the process of ascertaining certain characteristics of an elongated commodity 1 which constitutes a continuous cigarette rod having a rod-like filler 2 of shredded tobacco and a tubular envelope 3 of cigarette paper. The apparatus comprises a novel and improved resonator housing 4 including a main portion 6 and a cover or lid 8 detachably (such as threadedly) connected to the main portion. The main portion 6 is a relatively short cylinder which defines with the cover 8 a cylindrical internal chamber 7 having a symmetry axis at least substantially coinciding with the axis of the rod portion passing through the resonator housing 4. Such portion of the rod 1 is subjected to the action of microwaves which are supplied (particularly for the purpose of ascertaining the mass and/or the moisture content of the filler 2) by a least one antenna 16.

The cover 8 and its cover external tubular extension 8a define an inlet 21 of the housing 4, and the main portion 6 and its main portion external tubular extension 6a define an outlet 23 of the resonator housing 4. The internal chamber 7 is disposed between and communicates with the inlet 21 as well as with the outlet 23 of the housing. The external tubular extensions 8a and 6a are external extensions in contrast to the relatively short internal tubular extensions 8b, 6b which project into the chamber 7 to surround an elongated protective tube 13 which defines the actual path for successive increments of the continuous cigarette rod 1.

In accordance with a feature of the invention, the housing 4 (i.e., the main portion 6 and the cover 8) consists, at least in part, of a metallic material having a low (preferably very low) thermal expansion coefficient. For example, the housing 4 can be made of an alloy containing approximately 64% of iron and approximately 36% of nickel. Other metallic materials having similar thermal expansion characteristics can be utilized with equal or similar advantage. The ability of the metallic material of the resonator housing 4 to retain its selected optimum configuration and optimum dimensions contributes significantly to the accuracy of results of measurements of selected characteristic(s) of the rod-shaped commodities being advanced along the path defined by the protective tube 13.

The accuracy of measurements by resorting to an apparatus employing the improved resonator housing 4 is further enhanced by a temperature regulator for maintaining the temperature of the housing at least close to a preselected value in actual use of the apparatus. The illustrated temperature regulator includes a temperature sensor 9 (herinafter called thermometer) and at least one heating transistor 11 which receives signals from (i.e., which is controlled by) the thermometer 9. The transistor 11 can be of the type known as BUZ 80 distributed by Siemens. Heat which is being dissipated by the transistor 11 is utilized to raise the temperature of the housing 4 to maintain the temperature at a preselected value, preferably at a temperature which is above the temperature in the surrounding atmosphere. The temperature sensor 9 and heating transistor 11 have been found to be eminently suitable to maintain the temperature of the resonator housing 4 at least close to an optimum constant (preselected) value.

In accordance with a further important feature o f the invention, the internal surface of the resonator housing 4 is coated with a substance (e.g., in the form of a liner which surrounds the entire internal chamber 7) which reliably prevents or at least minimizes or delays corrosion of the housing around the internal chamber. At the same time, the liner at the internal surface 12 of the housing is highly satisfactory conductor of electric current. A metallic material which satisfies such requirements (resistance to corrosion and pronounced conductivity) is gold or another material exhibiting equivalent or similar characteristics. For example, a very thin film of gold can be deposited upon the internal surface 12 by resorting to a suitable vaporizing apparatus. Prevention of corrosion at the internal surface 12 of the resonator housing 4 is desirable and advantageous because such corrosion could adversely influence the accuracy of measurements being carried out regarding one or more selected characteristics of the moving rod 1. Satisfactory conductivity is desirable and advantageous because this prevents the development of the highly undesirable skin effect.

It is often preferred to apply a corrosion-resistant liner or film to a portion of or to entire external surface of the resonator housing 4. For example, at least a portion of such external surface can be provided with a thin or extremely thin liner of gold.

An important purpose of the aforementioned protective tube 13 is to mechanically seal the portion of the internal chamber 7 around the tube from those increments of the rod 1 which are being advanced through the housing 4 from the inlet (at the cover external tubular extension 8a) to the outlet (at the main portion external tubular extension 6a). This at least reduces the likelihood of contamination of the major part of the internal chamber 7 by particles of dirt (e.g., tobacco dust) being entrained by the external surface of the tubular wrapper 3. The presence of contaminants in the internal chamber 7 could adversely influence the accuracy of the results of measurements being carried out upon the rod 1. It is presently preferred to make the protective tube 13 of a synthetic plastic material, for example, of the polyaryletherketone group (PAEK), especially polyaryletheretherketone (PEEK).

The passage 13a defined by the rod-receiving portion of the protective tube 13 preferably diverges in a direction counter to the direction (indicated by the arrows 5) of advancement of the rod 1, i.e., in a direction away from the outlet 23 (at the main portion external tubular extension 6a) of the resonance housing 4. The diverging passage 13a is defined by a substantially funnel-shaped portion of the tube 13.

The purpose of the external extensions 6a, 8a of the main portion 6 and cover 8 of the resonator housing 4 is to prevent uncontrolled escape of microwaves from the internal chamber 7. The internal tubular extensions 6b, 8b (which are much shorter than the external tubular extensions 6a, 8a and extend into the chamber 7) serve a similar purpose. The internal tubular extensions 6b, 8b are optional but highly desirable.

The components for admitting microwaves from a generator (reference can be had to the aforementioned published European patent application Serial No. 0791 823 A2 or U.S. Pat. No. 6,163,158) into the chamber 7 include the antenna 16 which extends through an insulator 14 installed in the bottom end wall of the main portion 6 of the resonator housing 4. The components for conveying microwaves from the internal chamber 7 of the housing 4 includes an antenna 18 which extends through an insulator 17 also installed in the bottom end wall of the main housing portion 6. The evaluating circuit for microwaves issuing from the resonator housing 4 at 18 can be of the type disclosed in the commonly owned published German patent application Serial No. 197 34 978 A1 and in the corresponding United States patent application. One mode of evaluating the microwaves issuing from the internal chamber 7 while the tube 13 confines a length of the rod 1 and the microwaves issuing from the housing 4 while the tube 13 is empty is described in a preceding passage of this specification.

The improved resonator housing is susceptible of numerous additional modifications without departing from the spirit of the present invention. For example, the aforementioned percentages of iron and nickel in the alloy constituting a presently preferred metallic material of the housing 4 can depart from those (64% and 36%, respectively) mentioned hereinbefore. All that counts is to ensure that the thermal expansion coefficient of the resonator housing is sufficiently low to prevent excessive mechanical deformations in response to fluctuations of temperature in actual use of the apparatus. Excessive mechanical deformations are those which can adversely affect the accuracy of the measurements of certain characteristics of the elongated rod-shaped (including substantially rod-shaped) commodities. With this in mind, the material of the housing 4 can contain constituents other than iron and/or nickel, various percentages of iron and/or nickel, and/or iron, nickel and one or more additional elements.

The internal chamber 7 of the housing 4 which is shown in the drawing resembles a cylinder. However, it is equally possible to select another configuration which is at least substantially symmetrical with reference to the axis of the rod portion passing through the tube 13. For example, the internal chamber 7 can be replaced with one having a polygonal cross-sectional outline.

The liner or coating applied to the external surface or to the internal surface 12 of the housing 4 can consist of pure gold or of an alloy which contains gold. An advantage of pure gold is that a liner which coats the internal surface 12 and constitutes an extremely thin (such as vaporized) layer of pure gold suffices to ensure highly satisfactory and long-lasting resistance to corrosion as well as a highly satisfactory pronounced conductivity.

Without further analysis, the foregoing fully reveals the present invention so that others can, by applying current knowledge, readily adapt it for various applications without omitting features that, from the standpoint of prior art, fairly constitute essential characteristics of the generic and specific aspects of the above outlined contribution to the art of resonator housing for microwaves. Therefore, such adaptations should and are intended to be comprehended within the meaning and range of equivalence of the appended claims.

What is claimed is:

1. In an apparatus for ascertaining the characteristics of moving elongated rod-shaped commodities of the tobacco processing industry by exposure to microwaves, the improvement comprising: a metallic housing having an inlet for admission and an outlet for evacuation of commodities, wherein said housing has an internal chamber between said inlet and said outlet and said housing comprises an internal tubular extension provided at least at one of said inlet and said outlet, said internal tubular extension being disposed in said chamber and defining a portion of a path for movement of commodities from said inlet to said outlet.

* * * * *